United States Patent [19]

Yoshino et al.

[11] Patent Number: 4,607,031
[45] Date of Patent: Aug. 19, 1986

[54] NOVEL ETHYL BENZYLPHOSPHINATE DERIVATIVES, PROCESS FOR PRODUCTION THEREOF, AND THEIR USE AS CALCIUM ANTAGONIST

[75] Inventors: Koichiro Yoshino, Suita; Tominori Morita, Nishinomiya; Masaru Moriyama; Keizo Ito, both of Osaka; Goro Tsukamoto, Toyonaka, all of Japan

[73] Assignee: Kanebo Ltd., Tokyo, Japan

[21] Appl. No.: 737,037

[22] Filed: May 22, 1985

[30] Foreign Application Priority Data

Dec. 12, 1984 [JP] Japan .................... 59-263438
Apr. 13, 1985 [JP] Japan .................... 60-79093

[51] Int. Cl.$^4$ ............... A61K 31/675; C07F 9/65
[52] U.S. Cl. .................... 514/211; 514/212; 514/231; 514/321; 514/367; 546/24; 544/96; 548/111; 548/113
[58] Field of Search ............ 260/239.3 R; 544/96; 546/24; 548/113, 111; 514/211, 212, 231, 321, 367

[56] References Cited

U.S. PATENT DOCUMENTS 4,232,010  11/1980  Tsukamoto et al. .......... 548/113
4,434,162   2/1984  Tsukamoto et al. .......... 548/113

*Primary Examiner*—Robert T. Bond
*Attorney, Agent, or Firm*—Wenderoth, Lind & Ponack

[57] ABSTRACT

An ethyl benzylphosphinate derivative represented by the general formula (I)

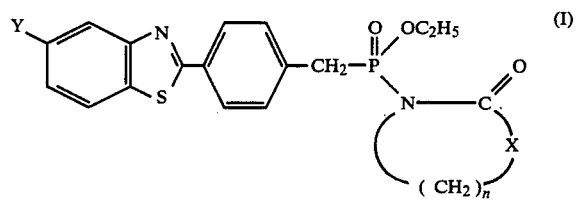

wherein Y represents a hydrogen or fluorine atom, X represents a methylene group or an oxygen atom, and n is 2, 3 or 4.

The said compounds can be produced by reacting a compound represented by the following formula (II)

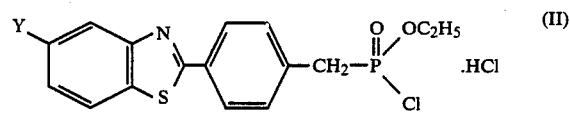

wherein Y is as defined above,
with a compound represented by the following formula (III)

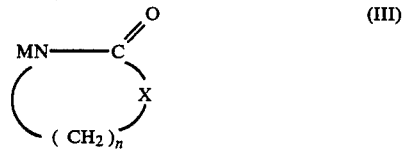

wherein X and n are as defined, and M is an alkali metal atom, in an inert medium. These compounds are useful as a calcium antagonist.

15 Claims, No Drawings

NOVEL ETHYL BENZYLPHOSPHINATE DERIVATIVES, PROCESS FOR PRODUCTION THEREOF, AND THEIR USE AS CALCIUM ANTAGONIST

This invention relates to novel ethyl benzylphosphinate derivatives, a process for production thereof, and a calcium antagonist comprising such a compound as an active ingredient.

Various compounds having calcium antagonistic activity are known. It is known, for example, that benzylphosphonic acid diester derivatives and analogous compounds thereof have excellent calcium antagonistic activity, coronary vasodilating activity and hypotensive activity (see U.S. Pat. Nos. 4,232,010 and 4,434,162). In particular, the results of a detailed pharmacological study of diethyl 4-(benzothiazol-2-yl)benzylphosphonate (compound A) represented by the following formula were reported [see T. Morita et al.: Arzneim.-Forsch./-Drug Res., 32 (II), 9, 1037–1088 (1982)].

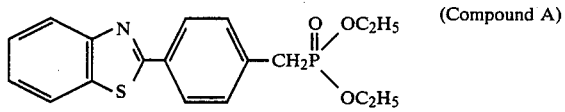
(Compound A)

It is an object of this invention to provide novel ethyl benzylphosphinate derivatives.

Another object of this invention is to provide novel ethyl benzylphosphinate derivatives which have calcium antagonistic activity and are effective for the prevention and treatment of ischemic heart diseases such as angina pectoris, myocardial infarction and arrhythmia and hypertension.

Still another object of this invention is to provide a process for producing the novel ethyl benzylphosphinate of this invention.

Yet another object of this invention is to provide a calcium antagonist comprising a novel ethyl benzylphosphinate derivative in accordance with this invention as an active ingredient.

Further objects and advantages of this invention will become apparent from the following description.

According to this invention, these objects and advantages are achieved by ethyl benzylphosphinate derivatives represented by the following general formula (I)

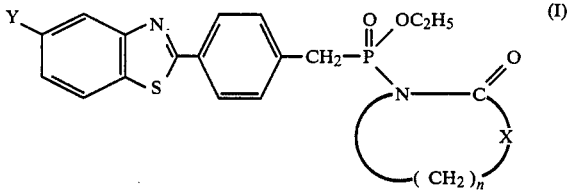
(I)

wherein Y represents a hydrogen or fluorine atom, X represents a methylene group or an oxygen atom, and n is 2, 3 or 4.

The general formula (I) encompasses the following 12 compounds.

(100) Ethyl 4-(benzothiazol-2-yl)benzyl-(2-oxopyrrolidino)phosphinate (Y=H, X=CH$_2$, n=2)
(101) Ethyl 4-(benzothiazol-2-yl)benzyl-(2-oxopiperidino)phosphinate (Y=H, X=CH$_2$, n=3)
(102) Ethyl 4-(benzothiazol-2-yl)benzyl-(2-oxohomopiperidino)phosphinate (Y=H, X=CH$_2$, n=4)
(103) Ethyl 4-(5-fluorobenzothiazol-2-yl)benzyl(2-oxopyrrolidino)phosphinate (Y=F, X=CH$_2$, n=2)
(104) Ethyl 4-(5-fluorobenzothiazol-2-yl)benzyl(2-oxopiperidino)phosphinate (Y=F, X=CH$_2$, n=3)
(105) Ethyl 4-(5-fluorobenzothiazol-2-yl)benzyl(2-oxohomopiperidino)phosphinate (Y=F, X=CH$_2$, n=4)
(106) Ethyl 4-(benzothiazol-2-yl)benzyl-(2-oxo-1,3-oxazolidino)phosphinate (Y=H, X=O, n=2)
(107) Ethyl 4-(benzothiazol-2-yl)benzyl-(2-oxotetrahydro-1,3-oxazino)phosphinate (Y=H, X=O, n=3)
(108) Ethyl 4-(benzothiazol-2-yl)benzyl-(2-oxo-1,3-oxazepino)phosphinate (Y=H, X=O, n=4)
(109) Ethyl 4-(5-fluorobenzothiazol-2-yl)benzyl(2-oxo-1,3-oxazolidino)phosphinate (Y=F, X=O, n=2)
(110) Ethyl 4-(5-fluorobenzothiazol-2-yl)benzyl(2-oxotetrahydro-1,3-oxazino)phosphinate (Y=F, X=O, n=3)
(111) Ethyl 4-(5-fluorobenzothiazol-2-yl)benzyl(2-oxo-1,3-oxazepino)phosphinate (Y=F, X=O, n=4)

According to this invention, the ethyl benzylphosphinate derivatives of general formula (I) can be produced by reacting a compound represented by the following formula (II)

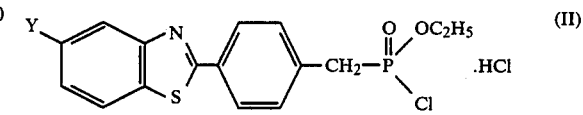
(II)

wherein Y is a hydrogen or fluorine atom, with a compound represented by the following formula (III)

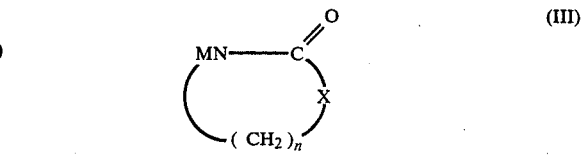
(III)

wherein
X is a methylene group or an oxygen atom,
M is an alkali metal atom and n is 2, 3 or 4, in the presence of an inert medium.

The compounds of formula (II) are novel compounds and can be produced by the method to be described below.

In formula (III), M represents an alkali metal atom such as sodium or potassium. The compounds of formula (III) can be produced by treating a compound corresponding to formula (III) in which M is hydrogen, with, for example, NaH in a conventional method.

The reaction of the compounds of formulae (II) and (III) is carried out in an inert medium. Suitable inert media are, for example, aromatic hydrocarbons such as benzene or toluene, ethers such as tetrahydrofuran or dioxane, and aprotic solvents such as acetonitrile or dimethylformamide.

Preferably, the reaction is carried out by using 1 to 3 moles of the compound of formula (III) per mole of the compound of formula (II). The reaction proceeds at 0° C. to room temperature, and the reaction time is usually about 1 to 24 hours. Preferably, the reaction is carried out in the presence of an organic amine such as triethylamine.

The compounds of formula (II) can be produced by heating a compound of the following formula (IV)-1

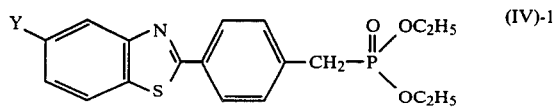

wherein Y is a hydrogen or fluorine atom,
and an excess of thionyl chloride, preferably in the presence of a catalytic amount of dimethylformamide, under reflux for a period of usually 2 to 4 hours.

The compounds of formula (IV)-1 in which Y is a fluorine atom are novel compounds. The compounds of formula (IV)-1 in which Y is a hydrogen atom are disclosed in the specification of U.S. Pat. No. 4,232,010.

The novel compounds of formula (IV)-1 in which Y is a fluorine atom can be produced in accordance with the following scheme.

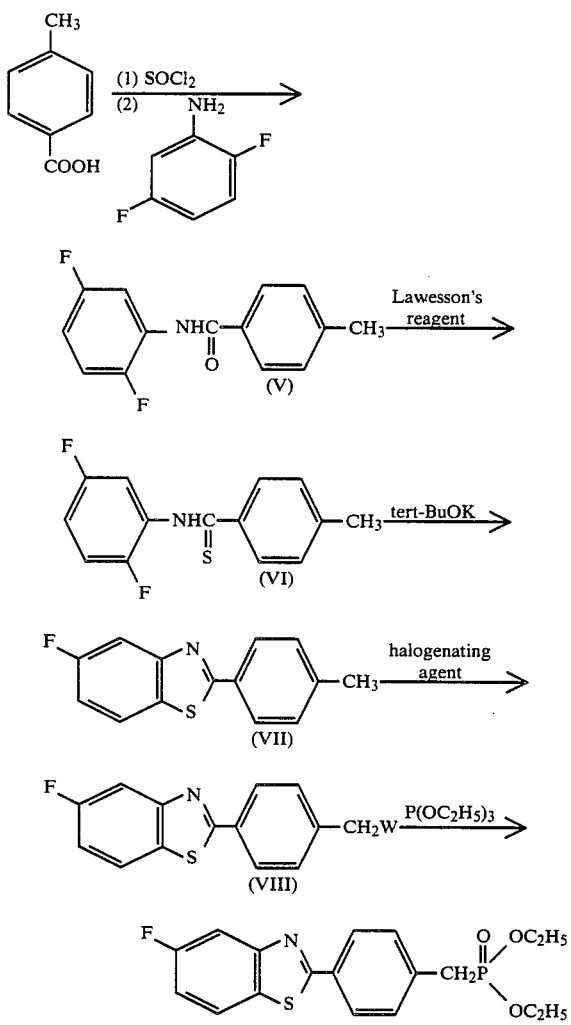

(In the above scheme, W represents a halogen atom.)

First, p-toluic acid is converted to an acid chloride with thionyl chloride. The acid chloride is reacted with 2,5-difluoroaniline to form 4-methyl-2′,5′-difluorobenzanilide (V). The compound (V) is then reacted with 2,4-bis(4-methoxyphenyl)-1,3-dithia-2,4-diphosphethane-2,4-disulfide (Lawesson's reagent) to form 4-methyl-2′,5′-difluorobenzothioanilide (VI) which is then reacted with potassium tert-butoxide to form 2-(4-methylphenyl)-5-fluorobenzothiazole (VII). The compound (VII) is then reacted with a halogenating agent such as N-bromosuccinimide, N-chlorosuccinimide or bromine to form a compound (VIII). Finally, the compound (VIII) is reacted with an excess of triethyl phosphite to produce the compound of formula (IV)-1 in which Y is a fluorine atom.

The compound of formula (II) can be produced by reacting a monoethyl ester represented by the following formula (IV)-2.

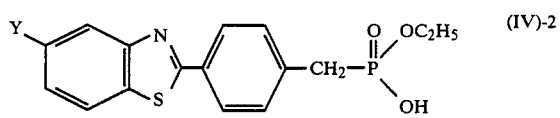

wherein Y is a hydrogen or fluorine atom,
with an excess of thionyl chloride in the absence of solvent or in a solvent such as chloroform or carbon tetrachloride, preferably in the presence of a catalytic amount of dimethylformamide, at a temperature ranging from room temperature to the boiling point of the solvent for a period of usually 1 to 8 hours.

The compounds of formula (IV)-2 in which Y is a fluorine atom are novel compounds. The compound of formula (IV)-2 in which Y is a hydrogen atom is disclosed in the specification of U.S. Pat. No. 4,434,162. The compound of formula (IV)-2 in which Y is a fluorine atom can be produced by partially hydrolyzing the compound of formula (IV)-1 in which Y is a fluorine atom.

Investigations of the present inventors have shown that the compounds of formula (I) provided by this invention have calcium antagonistic activity, strong coronary vasodilating activity and hypotensive activity and their toxicity is low; and therefore that these compounds are useful in the treatment of ischemic heart diseases such as angina pectoris, myocardial infarction and arrhythmia, and hypertension.

Accordingly, the present invention provides a calcium antagonist comprising an ethyl benzylphosphinate derivatives of formula (I) as an active ingredient.

The compounds of formula (I) have excellent absorbability in oral administration and are normally used in orally administrable forms.

For oral administration, the compounds of formula (I) may be formulated in a customary manner into tablets, granules or powders together with ordinary pharmaceutical additives, for example an excipient such as lactose, synthetic aluminum silicate, glucose or mannitol, a disintegrant such as carboxymethyl cellulose or sodium arginate, a lubricant such as magnesium stearate or talc, or a binder such as corn starch or polyvinyl pyrrolidone, or may be used as capsules prepared by filling such granules or powders into suitable capsules.

The dosage of the compound of formula (I) provided by this invention varies depending upon the condition, body weight, age, etc. of the patient. Usually, it is 50 to 250 mg per day per adult, either at a time or in 2 or 3 divided portions.

The pharmaceutical effects of the compounds of formula (I) will be shown below by animal experiments.

1. Calcium Antagonistic Activity

Test Compounds (100) Ethyl 4-(benzothiazol-2-yl)benzyl-(2-oxopyrrolidino)phosphinate (Y=H, X=CH$_2$, n=2)
(101) Ethyl 4-(benzothiazol-2-yl)benzyl-(2-oxopiperidino)phosphinate (Y=H, X=CH$_2$, n=3)
(102) Ethyl 4-(benzothiazol-2-yl)benzyl-(2-oxohomopiperidino)phosphinate (Y=H, X=CH$_2$, n=4)
(103) Ethyl 4-(5-fluorobenzothiazol-2-yl)benzyl-(2-oxopyrrolidino)phosphinate (Y=F, X=CH$_2$, n=2)
(104) Ethyl 4-(5-fluorobenzothiazol-2-yl)benzyl-(2-oxopiperidino)phosphinate (Y=F, X=CH$_2$, n=3)
(105) Ethyl 4-(5-fluorobenzothiazol-2-yl)benzyl-(2-oxohomopiperidino)phosphinate (Y=F, X=CH$_2$, n=4)
(109) Ethyl 4-(5-fluorobenzothiazol-2-yl)benzyl-(2-oxo-1,3-oxazolidino)phosphinate (Y=F, X=O, n=2)
Compound A (control) given hereinabove

Testing Method

Male guinea pigs, weighing 405–500 g, were stunned and bled. The taenia preparation in a length of about 2 cm was isolated from caecum and suspended in an organ bath filled with Ca$^{2+}$-free Ringer-Lock solution (composition, mM: NaCl 154, KCl 5.6, NaHCO$_3$ 2.3, glucose 5.5). The bathing solution was maintained at 30±1° C. and bubbled with air. The contractile response was recorded using an isotonic transducer (TD-112S made by Nihon Kohden Co., Ltd.) under a load of 0.5 g.

After sufficient incubation to remove Ca$^{2+}$, the bathing solution was replaced by Ca$^{2+}$-free, K$^+$-rich Ringer-Lock solution (composition, mM: NaCl 59.6, KCl 100, NaHCO$_3$ 2.3, glucose 5.5). An aqueous solution of CaCl$_2$ (0.03–100 mm) was cumulatively added to the bathing solution every 10 minutes, and a concentration-response curve for Ca$^{2+}$ was obtained. After washing out Ca$^{2+}$ the same procedure as above was carried out in the presence of each of the test compounds, and the pA$_2$ value of the calcium antagonistic activity was calculated from the difference between the concentration-response curves obtained in the absence and presence of the test compound.

Each of the test compounds was dissolved in 5% ethanol and added to the bathing solution (the final concentration of ethanol was 0.05%).

Test Results

The results are shown in Table 1.

TABLE 1

| Test compound | Cases | Calcium antagonistic activity (pA$_2$ values, mean ± standard error) |
|---|---|---|
| 100 | 10 | 7.53 ± 0.095 |
| 101 | 10 | 7.45 ± 0.105 |
| 102 | 10 | 7.46 ± 0.100 |
| 103 | 5 | 7.73 ± 0.113 |
| 104 | 5 | 7.68 ± 0.101 |
| 105 | 5 | 7.73 ± 0.146 |
| 109 | 5 | 7.69 ± 0.155 |
| Compound A (control) | 10 | 7.21 ± 0.079 |

2. Coronary Vasodilating Activity and Hypotensive Activity

Test Compounds

The same compounds as used in 1 were tested.

Testing Method

Coronary vasodilating activity was examined by measuring the amount of coronary blood flow as an index. Mongrel dogs weighing 10 to 19 kg were anesthetized by intravenously injecting sodium pentobarbital (30 mg/kg) and thoracotomized at the 5th left intercostal space under artificial ventilation. After incision of the pericardiac membrane, a flow probe was placed at the circumflex banch of the left coronary artery and led to an electromagnetic flow meter (MFV-2100 made by Nihon Kohden Co., Ltd.). The systemic blood pressure of the animals was measured by a pressure transducer (MPU-0.5 made by Nihon Kohden Co., Ltd.) connected to the cannulated left femoral artery. The coronary blood flow and the systemic blood pressure were recorded on a polygraph (RM-85 made by Nihon Kohden Co., Ltd.). Each of the test compounds was dissolved in ethanol/saline solution (1/1, V/V) and injected into the femoral vein.

Each of the test compounds was administered in a dose of 0.03 to 0.3 mg/kg, and doses which increase the coronary blood flow by 75% (CBF-ID$_{75}$) and decrease the mean systemic blood pressure by 15% (MDP-DD$_{15}$) were calculated from the regression lines.

Test Results

The results are shown in Table 2.

TABLE 2

| Test compounds | Cases | Coronary blood flow increasing activity CBF-ID$_{75}$ (mg/kg) | Mean systemic blood pressure lowering activity MBP-DD$_{15}$ (mg/kg) |
|---|---|---|---|
| 100 | 8 | 0.0440 | 0.0387 |
| 101 | 8 | 0.0600 | 0.0582 |
| 102 | 8 | 0.0573 | 0.0540 |
| 103 | 5 | 0.0644 | 0.0901 |
| 104 | 5 | 0.0647 | 0.0629 |
| 105 | 5 | 0.0583 | 0.0712 |
| 109 | 5 | 0.0615 | 0.0748 |
| Compound A (control) | 8 | 0.1160 | 0.1584 |

3 Acute Toxicity

Test Compounds

The same compounds as used in 1 were tested.

Testing Method

Each of the test compounds was suspended in 0.5% carboxymethyl cellulose, and orally administered to ddY-strain male mice (body weight 18–24 g; five per group), and the mortality of the animals was observed for 7 days.

Test Results

The results are shown in Table 3.

TABLE 3

| Test compounds | Acute toxicity LD$_{50}$ (mg/kg) |
| --- | --- |
| 100 | >1000 |
| 101 | >1000 |
| 102 | >1000 |
| 103 | >1000 |
| 104 | >1000 |
| 105 | >1000 |
| 109 | >1000 |
| Compound A (control) | >1000 |

The foregoing results of the pharmacological tests clearly demonstrate that the compounds of formula (I) provided by this invention have better calcium antagonistic activity, coronary vasodilating activity and hypotensive activity than compound A used as a control and their toxicity is low, and therefore that these compounds are useful for the treatment of ischemic heart diseases such as angina pectoris, myocardial infarction and arrhythmia, and hypertension.

The following examples illustrate the present invention more specifically.

EXAMPLE 1

Production of ethyl 4-(benzothiazol-2-yl)benzyl(2-oxopyrrolidino)phosphinate (compound 100)

Ethyl hydrogen 4-(benzothiazol-2-yl)benzylphosphonate (5.0 g) and 40 g of thionyl chloride were mixed, and one drop of dimethylformamide was added. The mixture was refluxed for 2.5 hours. After the reaction, the excess of thionyl chloride was evaporated under reduced pressure to give quantitatively the corresponding phosphonochloridate hydrochloride as a pale yellow powder.

NMR (CDCl$_3$, δ ppm): 1.1–1.4 (3H, t), 3.0–3.4 (2H, d), 3.7–4.3 (2H, m), 7.3–7.6 (4H, m), 7.8–8.2 (4H, m).

The resulting phosphonochloridate hydrochloride was suspended in 100 ml of tetrahydrofuran, and a solution of 6.0 g of triethylamine in 25 ml of tetrahydrofuran was added dropwise under ice cooling. 1.5 g of 2-pyrrolidone was dissolved in 25 ml of tetrahydrofuran, and 0.60 g of sodium hydride (60%) was added to prepare a sodium salt of 2-pyrrolidone. The sodium salt of 2-pyrrolidone was added to the solution prepared above. The mixture was stirred at room temperature for 2 hours, and the solvent was evaporated under reduced pressure. The residue was subjected to silica gel column chromatography (developing solvent: ethyl acetate), and recrystallized from ethyl acetate to give 4.5 g (yield 75%) of the captioned compound as colorless platelike crystals.

Melting point: 128°–130° C.

NMR (CDCl$_3$, δ ppm): 1.3–1.5 (3H, t), 1.7–2.2 (2H, m), 2,3–2.6 (2H, m), 3.1–3.8 (4H, m), 3.9–4.4 (2H, m), 7.3–7.6 (4H, m), 7.8–8.1 (4H, m).

Elemental analysis for C$_{20}$H$_{21}$N$_2$O$_3$PS: Calculated (%): C, 59.99; H, 5.29; N, 7.00. Found (%): C, 59.68; H, 5.13; N, 6.93.

EXAMPLE 2

Production of ethyl 4-(benzothiazol-2-yl)benzyl(2-oxopiperidino)phosphinate (compound 101)

Ethyl hydrogen 4-(benzothiazol-2-yl)benzylphosphonate (3.3 g) and 25 g of thionyl chloride were mixed, and one drop of dimethylformamide was added. The mixture was refluxed for 3 hours. After the reaction, the excess of thionyl chloride was evaporated under reduced pressure to give quantitatively the corresponding phosphonochloridate hydrochloride as a pale yellow powder. The resulting phosphonochloridate hydrochloride was suspended in 50 ml of tetrahydrofuran, and a solution of 4.0 g of triethylamine in 20 ml of tetrahydrofuran was added dropwise under ice cooling. A sodium salt of δ-valerolactam obtained by dissolving 1.2 g of δ-valerolactam in 20 ml of tetrahydrofuran and adding 0.4 g of sodium hydride (60%) was added to the resulting solution. The mixture was stirred at room temperature for 2 hours, and the solvent was evaporated under reduced pressure. The residue was subjected to silica gel column chromatography (developing solvent: ethyl acetate), and recrystallized from ethyl acetate to give 1.9 g (yield 46%) of the captioned compound as colorless plate-like crystals.

Melting point: 107°–109° C.

NMR (CDCl$_3$, δ ppm): 1.3–1.6 (3H, t), 1.6–1.9 (4H, m), 2.3–2.6 (2H, m), 3.1–3.9 (4H, m), 3.9–4.4 (2H, m), 7.3–7.6 (4H, m), 7.8–8.1 (4H, m).

Elemental analysis for C$_{21}$H$_{23}$N$_2$O$_3$PS: Calculated (%): C, 60.86; H, 5.59; N, 6.76. Found (%): C, 60.77; H, 5.76; N, 6.78.

When in the above procedure, the recrystallization was carried out by using cyclohexane instead of ethyl acetate, the captioned compound was obtained as colorless needle-like crystals having a melting point of 121° to 123° C.

EXAMPLE 3

Production of ethyl 4-(benzothiazol-2-yl)benzyl(2-oxohomopiperidino)phosphinate (compound 102)

Ethyl hydrogen 4-(benzothiazol-2-yl)benzylphosphonate (6.6 g) and 50 g of thionyl chloride were mixed, and one drop of dimethylformamide was added. The mixture was refluxed for 3 hours. After the reaction, the excess of thionyl chloride was evaporated under reduced pressure to obtain quantitatively the corresponding phosphonochloridate hydrochloride as a pale yellow powder. The resulting phosphonochloridate hydrochloride was suspended in 100 ml of tetrahydrofuran, and a solution of 8.0 g of triethylamine in 40 ml of tetrahydrofuran was added dropwise under ice cooling. A sodium salt of ε-caprolactam prepared by dissolving 4.5 g of ε-caprolactam in 40 ml of tetrahydrofuran and adding 0.8 g of sodium hydride (60%) was added to the solution prepared above, and the mixture was stirred at room temperature for 2 hours. The solvent was evaporated under reduced pressure, and the residue was subjected to silica gel column chromatography (developing solvent: ethyl acetate), and recrystallized from ethyl acetate to give 5.1 g (yield 60%) of the captioned compound as colorless scale-like crystals.

Melting Point: 125°–127° C.

NMR (CDCl$_3$, δ ppm): 0.8–1.8 (9H, m), 2.4–2.7 (2H, m), 3.3–4.3 (6H, m), 7.3–7.6 (4H, m), 7.8–8.1 (4H, m).

Elemental analysis for C$_{22}$H$_{25}$N$_2$O$_3$PS: Calculated (%): C, 61.67; H, 5.88; N, 6.54. Found (%): C, 61.84; H, 5.97; N, 6.55.

EXAMPLE 4

Production of ethyl 4-(5-fluorobenzothiazol-2-yl)-benzyl-(2-oxopyrrolidino)phosphinate (compound 103)

Diethyl 4-(5-fluorobenzothiazol-2-yl)benzylphosphonate (4.2 g) prepared as shown below was mixed with 40 ml of thionyl chloride, and one drop of dimethylformamide was added. The mixture was refluxed for 3 hours. After the reaction, the excess of thionyl chloride was evaporated under reduced pressure to give quantitatively the corresponding phosphonochloridate hydrochloride as a pale yellow powder.

NMR (DMSO-$d_6$, δ ppm): 1.1–1.3 (3H, t), 3.0–3.4 (2H, d), 3.7–4.3 (2H, m), 7.1–7.6 (3H, m) 7.7–8.3 (4H, m).

The resulting phosphonochloridate hydrochloride was suspended in 50 ml of tetrahydrofuran, and a solution of 1.0 g of triethylamine in 5 ml of tetrahydrofuran was added dropwise under ice cooling. A sodium salt of 2pyrrolidone prepared by dissolving 0.85 g of 2-pyrrolidone in 15 ml of tetrahydrofuran and adding 0.40 g of sodium hydride (60%) was added to the solution prepared above. The mixture was stirred at 0° C. for 30 minutes, and 300 ml of water was added. The mixture was extracted three times with 300 ml of ether. The ethereal layers were dried over magnesium sulfate, and evaporated to dryness under reduced pressure. The residue was recrystallized from cyclohexane to give 2.2 g (yield 49%) of the captioned compound as colorless needle-like crystals.

Melting point: 142°–144° C.

NMR (CDCl$_3$, δ ppm): 1.3–1.5 (3H, t), 1.7–2.2 (2H, m), 2.3–2.6 (2H, m), 3.1–3.8 (4H, m), 3.9–4.4 (2H, m), 7.0–7.5 (3H, m), 7.6–8.1 (4H, m).

Elemental analysis for $C_{20}H_{20}FN_2O_3PS$: Calculated (%): C, 57.41; H, 4.82; N, 6.70. Found (%): C, 57.65; H, 4.74; N, 6.66.

Production of diethyl 4-(5-fluorobenzothiazol-2-yl)-benzylphosphonate (1) Production of 4-methyl-2',5'-difluorobenzanilide p-Toluic acid (26.4 g) and 46 g of thionyl chloride were mixed, and one drop of dimethylformamide was added. The mixture was refluxed for 1 hour. The reaction mixture was evaporated to dryness under reduced pressure. The residue was dissolved in 30 ml of dry tetrahydrofuran, and the solution was added dropwise onto 155 ml of a pyridine solution of 25 g of 2,5-difluoroaniline over the course of 40 minutes. The mixture was stirred at room temperature for 2 hours, and the reaction mixture was poured into 1300 ml of water. The precipitated colorless crystalline powder was collected by filtration, and dried to give 44.0 g of crude crystals of the captioned compound. Recrystallization from cyclohexane gave the captioned compound as colorless scale-like crystals.

Melting point: 108°–110° C.

(2) Production of 4-methyl-2',5'-difluorobenzothioanilide 36.7 g of 4-methyl-2',5'-difluorobenzanilide was dissolved in 170 ml of toluene, and 36 g of Lawesson's reagent was added. The mixture was refluxed for 1 hour. The reaction mixture was evaporated to dryness under reduced pressure. The residue was recrystallized from 100 ml of benzene to give 35.0 g of the captioned compound as yellow needle-like crystals.

Melting point: 118°–121° C.

(3) Production of 2-(4-methylphenyl)-5-fluorobenzothiazole

A solution of 35.0 g of 4-methyl-2',5'-difluorobenzothioanilide in 80 ml of dimethylformamide was added dropwise to a suspension of 16.0 g of potassium tert-butoxide in 80 ml of dimethylformamide under ice cooling over the course of 15 minutes. The reaction mixture was heated, and reacted at 140° C. for 3 hours. The reaction mixture was allowed to cool to room temperature and poured into 1500 ml of water. The preceipitated colorless crystalline power was collected by filtration, and dried to give 31.6 g of crude crystals of the captioned compound. Recrystallization from n-hexane gave the captioned compound as colorless plate-like crystals.

Melting point: 120°–112° C.

(4) Productuon of 2-(4-bromomethylphenyl-5-fluorobenzothiazole 31.6 g of 2-(4-methylphenyl)-5-fluorobenzothiazole was dissolved in 660 ml of carbon tetrachloride, and 23.1 g of N-bromosuccinimide and 700 mg of benzoyl peroxide were added. The mixture was refluxed for 6 hours. The reaction mixture was cooled to room temperature, and the insoluble materials were separated by filtration. The filtrate was concentrated to a volume of 100 ml under reduced pressure. The precipitated crystals were collected by filtration to give 31.0 g of the captioned compound as crude crystals. Recrystallization from carbon tetrachloride gave the captioned compound as colorless platelike crystals.

Melting point: 138°–141° C.

(5) Production of diethyl 4-(5-fluorobenzothiazol-2-yl)-benzylphosphonate

Triethyl phosphite (50.0 g) was added to 31.0 g of 2-(4-bromomethylphenyl)-5-fluorobenzothiazole, and the mixture was reacted at 150° to 160° C. for 15 minutes under a stream of nitrogen. The reaction mixture was allowed to cool to room temperature, and 100 ml of n-hexane was added. The precipitated crystals were collected by filtration and dried to give 39.0 g of crude crystals. Recrystallization from a mixture of ethyl acetate and cyclohexane gave 30.0 g of the captioned compound as colorless needle-like crystals.

Melting point: 129°–132° C.

EXAMPLE 5

Production of ethyl 4-(5-fluorobenzothiazol-2-yl)benzyl-(2-oxopiperidino)-phosphinate (compound 104)

Diethyl 4-(5-fluorobenzothiazol-2-yl)benzylphosphonate (4.2 g) and 40 ml of thionyl chloride were mixed, and one drop of dimethylformamide was added. The mixture was refluxed for 3 hours. After the reaction, the excess of thionyl chloride was evaporated under reduced pressure to give quantitatively the corresponding phosphonochloridate hydrochloride as a pale yellow powder. The resulting phosphonochloridate hydrochloride was suspended in 50 ml of tetrahydrofuran, and a solution of 1.0 g of triethylamine in 5 ml of tetrahydrofuran was added dropwise to the suspension under ice cooling. A sodium salt of δ-valerolactam prepared by dissolving 1.0 g of δ-valerolactam in 30 ml of tetrahydrofuran and adding 0.4 g of sodium hydride (60%) was added to the solution prepared above. The mixture was stirred at 0° C. for 2 hours, and 300 ml of water was added. The mixture was extracted three times with 300 ml of ether. The ethereal layers were dried over magnesium sulfate and evaporated to dryness under reduced pressure. The residue was recrystallized from cyclohexane to give 1.2 g (yield 28%) of the captioned compound as colorless scale-like crystals.

Melting point: 144°–148° C.

NMR (CDCl$_3$, δ ppm): 1.3–1.6 (3H, t), 1.6–1.9 (4H, m), 2.3–2.6 (2H, m), 3.1–3.9 (4H, m), 3.9–4.4 (2H, m), 7.0–7.5 (3H, m), 7.6–8.1 (4H, m).

Elemental analysis for $C_{21}H_{22}FN_2O_3PS$: Calculated (%): C, 58.32; H, 5.13; N, 6.48. Found (%): C, 58.55; H, 5.27 N, 6.51.

EXAMPLE 6

Production of ethyl 4-(5-fluorobenzothiazol-2-yl)benzyl-(2-oxohomopiperidino)phosphinate (compound 105)

Diethyl 4-(5-fluorobenzothiazol-2-yl)benzylphosphonate (10.0 g) and 70 ml of thionyl chloride were mixed, and one drop of dimethylformamide was added. The mixture was refluxed for 3 hours. After the reaction, the excess of thionyl chloride was evaporated under reduced pressure to give quantitatively the corresponding phosphonochloridate hydrochloride as a pale yellow powder. The resulting phosphonochloridate hydrochloride was suspended in 100 ml of tetrahydrofuran, and a solution of 2.4 g of triethylamine in 10 ml of tetrahydrofuran was added dropwise under ice cooling. A sodium salt of ε-caprolactam prepared by dissolving 2.7 g of ε-caprolactam in 60 ml of tetrahydrofuran and adding 0.96 g of sodium hydride (60%) was added to the solution prepared above. The mixture was stirred at room temperature for 6 hours, and 600 ml of water was added. The mixture was extracted three times with 400 ml of ether. The ethereal layers were dried over magnesium sulfate, and evaporated to dryness under reduced pressure. The residue was subjected to silica gel column chromatography (developing solvent: ethyl acetate), and recrystallized from cyclohexane to give 3.8 g (yield 36%) of the captioned compound as colorless needle-like crystals.

Melting point: 108°–125° C.

NMR (CDCl$_3$, δ ppm): 0.8–1.8 (9H, m), 2.4–2.7 (2H, m), 3.3–4.3 (6H, m), 7.1–7.5 (3H, m), 7.6–8.1 (4H, m).

Elemental analysis for $C_{22}H_{24}FN_2O_3PS$: Calculated (%): C, 59.18; H, 5.42; N, 6.27. Found (%): C, 59.28; H, 5.55; N, 6.22.

EXAMPLE 7

Production of 4-(5-fluorobenzothiazol-2-yl)-benzyl-(2-oxo-1,3-oxazolidino)phosphinate (compound 109)

Diethyl 4-(5-fluorobenzothiazol-2-yl)benzylphosphonate (8.0 g) and 70 ml of thionyl chloride were mixed, and one drop of dimethylformamide was added. The mixture was refluxed for 3 hours. After the reaction, the excess of thionyl chloride was evaporated under reduced pressure to give quantitatively the corresponding phosphonochloridate hydrochloride as a pale yellow powder. The resulting phosphonochloridate hydrochloride was suspended in 100 ml of tetrahydrofuran, and a solution of 2.1 g of triethylamine in 10 ml of tetrahydrofuran was added dropwise under ice cooling. A sodium salt of 2-oxazolidone prepared by dissolving 1.8 g of 2-oxazolidone in 60 ml of tetrahydrofuran and adding 0.84 g of sodium hydride (60%) was added to the solution prepared above. The mixture was stirred at 0° C. for 2 hours, and 600 ml of water was added. The mixture was extracted three times with 400 ml of ether. The ethereal layers were dried over magnesium sulfate, and evaporated to dryness under reduced pressure. The residue was subjected to silica gel column chromatography (developing solvent: ethyl acetate), and recrystallized from a mixture of cyclohexane and ethyl acetate to give 4.0 g (yield 45%) of the captioned compound as colorless scalelike crystals.

Melting point: 163°–167° C.

NMR (CDCl$_3$, δ ppm): 1.3–1.5 (3H, t), 3.2–4.5 (8H, m), 7.0–7.6 (3H, m), 7.6–8.1 (4H, m).

Elemental analysis for $C_{19}H_{18}FN_2O_4PS$: Calculated (%): C, 54.28; H, 4.32; N, 6.66. Found (%): C, 54.45; H, 4.32; N, 6.81.

EXAMPLE 8

Preparation of tablets:

| Ingredients | Parts by weight |
| --- | --- |
| Compound 100 (Example 1) | 60.0 |
| Lactose | 54.0 |
| Corn starch | 30.0 |
| Hydroxypropyl cellulose | 5.0 |
| Crystalline cellulose | 30.0 |
| Magnesium stearate | 1.0 |

Operation:

A mixture of the compound 100, lactose, corn starch and hydroxypropyl cellulose was kneaded with water to form granules. After drying, the granules were mixed with crystalline cellulose and magnesium stearate, and tableted into tablets each weighing 180 mg.

EXAMPLE 9

Preparation of capsules:

| Ingredient | Parts by weight |
| --- | --- |
| Compound 100 (Example 1) | 60.0 |
| Lactose | 50.0 |
| Corn starch | 30.0 |

Operation:

The above ingredients were mixed, and the resulting powdery mixture was filled into #2 capsules each in an amount of 140 mg.

EXAMPLES 10–21

Tablets and capsules were prepared in the same way as in Examples 8 and 9, respectively, except that compounds 101 to 105 (Examples 2 to 6), and 109 (Example 7) were used instead of the compound 100 (Example 1).

What is claimed is:

1. An ethyl benzylphosphinate, compound represented by the formula (I)

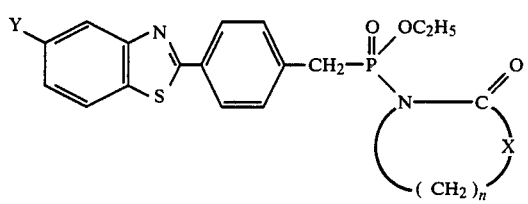

(I)

wherein Y represents a hydrogen or fluorine atom, X represents a methylene group or an oxygen atom, and n is 2, 3 or 4.

2. The compound of claim 1 which is ethyl 4-(benzothiazol-2-yl)benzyl-(2-oxopyrrolidino)phosphinate.

3. The compound of claim 1 which is ethyl 4-(benzothiazol-2-yl)benzyl-(2-oxopiperidino)phosphinate.

4. The compound of claim 1 which is ethyl 4-(benzothiazol-2-yl)benzyl-(2-oxohomopiperidino)phosphinate.

5. The compound of claim 1 which is ethyl 4-(5-fluorobenzothiazol-2-yl)benzyl-(2-oxopyrrolidino)-phosphinate.

6. The compound of claim 1 which is ethyl 4-(5-fluorobenzothiazol-2-yl)benzyl-(2-oxopiperidino)phosphinate.

7. The compound of claim 1 which is ethyl 4-(5-fluorobenzothiazol-2-yl)benzyl-(2-oxohomopiperidino)-phosphinate.

8. The compound of claim 1 which is ethyl 4-(benzothiazol-2-yl)benzyl-(2-oxo-1,3-oxazolidino)phosphinate.

9. The compound of claim 1 which is ethyl 4-(benzothiazol-2-yl)benzyl-(2-oxo-tetrahydro-1,3-oxazino)-phosphinate.

10. The compound of claim 1 which is ethyl 4-(benzothiazol-2-yl)benzyl-(2-oxo-1,3-oxazepino)phosphinate.

11. The compound of claim 1 which is ethyl 4-(5-fluorobenzothiazol-2-yl)benzyl-(2-oxo-1,3-oxazolidino)-phosphinate.

12. The compound of claim 1 which is ethyl 4-(5-fluorobenzothiazol-2-yl)benzyl-(2-oxo-tetrahydro-1,3-oxazino)phosphinate.

13. The compound of claim 1 which is ethyl 4-(5-fluorobenzothiazol-2-yl)benzyl-(2-oxo-1,3-oxazepino)-phosphinate.

14. A process for producing an ethyl benzylphosphinate compound represented by the following formula (I)

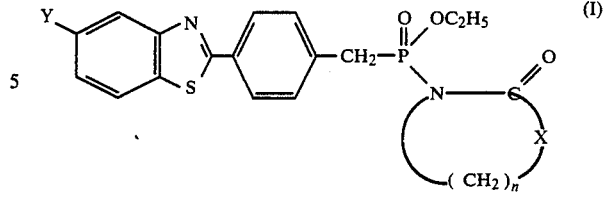

(I)

wherein X represents a methylene group or an oxygen atom, Y represents a hydrogen or fluorine atom, and n is 2, 3 or 4, which comprises reacting a compound represented by the following formula (II)

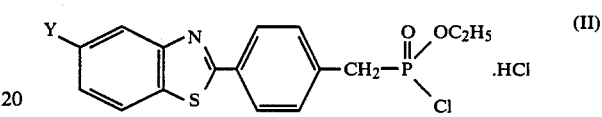

(II)

wherein Y is as defined above, with a compound represented by the following formula (III)

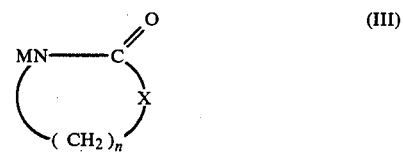

(III)

wherein X and n are as defined, and M is an alkali metal atom, in an inert medium.

15. A calcium antagonist composition comprising a calcium antagonist effective amount of an ethyl benzylphosphinate compound represented by the following formula (I)

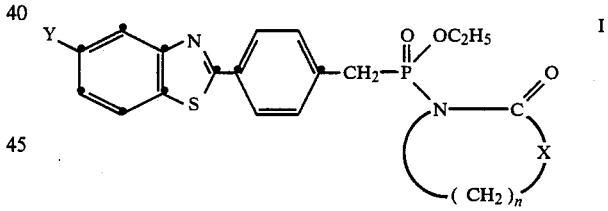

I wherein Y represents a hydrogen or fluorine atom, X represents a methylene group or an oxygen atom, and n is 2, 3 or 4, in admixture with a pharmaceutically acceptable carrier therefor.

* * * * *